United States Patent [19]

Fleck et al.

[11] 4,025,507
[45] May 24, 1977

[54] BIS-(TRIAZINYLAMINO) STILBENE COMPOUNDS

[75] Inventors: Fritz Fleck, Bottmingen; Hans-Rudolf Schmid, Riehen, both of Switzerland

[73] Assignee: Sandoz Ltd., Basel, Switzerland

[22] Filed: June 25, 1974

[21] Appl. No.: 483,009

[30] Foreign Application Priority Data

July 2, 1973 Switzerland .............. 9599/73

[52] U.S. Cl. ............... 260/240 B; 252/301.23; 427/158
[51] Int. Cl.[2] ............... C07D 403/02
[58] Field of Search ............... 260/240 B

[56] References Cited

UNITED STATES PATENTS

| 3,018,287 | 1/1962 | Fleck ............... 260/240 B |
| 3,479,349 | 11/1969 | Allison et al. ............... 260/240 B |
| 3,589,921 | 6/1971 | Allison et al. ............... 260/240 B |
| 3,723,425 | 3/1973 | Ackerman et al. ............... 252/301.2 W |
| 3,740,341 | 6/1973 | Brocklehurst ............... 260/240 B |
| 3,757,010 | 9/1973 | Balzer et al. ............... 260/240 B |

FOREIGN PATENTS OR APPLICATIONS

| 522,082 | 6/1972 | Switzerland |
| 1,313,469 | 4/1973 | United Kingdom |

OTHER PUBLICATIONS

Loffelman Chem. Abstracts 75(1971), No. 152986.
Farbenfabriken Chem. Abstracts 74 (1971), No. 43527.
Ackermann Chem. Abstracts 75, (1971), No. 50427.

Primary Examiner—Arthur P. Demers
Attorney, Agent, or Firm—Gerald D. Sharkin; Richard E. Vila; Joseph J. Borovian

[57] ABSTRACT

Disclosed are compounds of formula I,

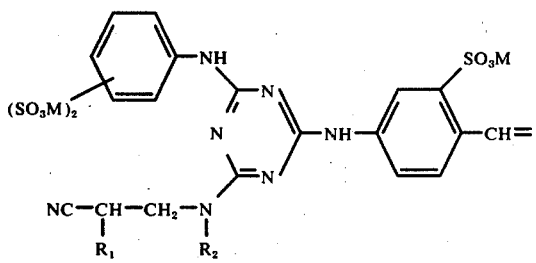
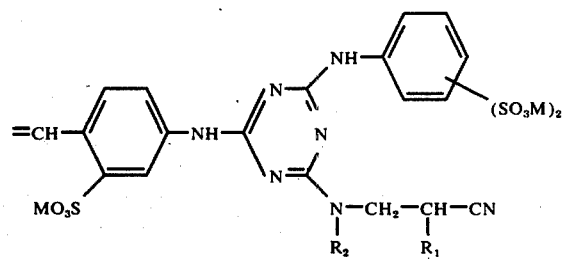

in which
the $R_1$'s are the same and signify hydrogen or methyl,
the $R_2$'s are the same and signify hydrogen; $C_{1-6}$alkyl; cyclohexyl, unsubstituted or substituted by up to three $C_{1-6}$alkyl radicals; or benzyl, unsubstituted or substituted by up to two substituents selected from halogen, $C_{1-6}$alkoxy and $C_{1-6}$alkyl, and
the M's signify hydrogen or a nonchromophoric cation, their production and use as optical brightening agents for cellulosic substrates, particularly paper substrates.

8 Claims, No Drawings

BIS-(TRIAZINYLAMINO) STILBENE COMPOUNDS

The invention relates to stilbene compounds.
The invention provides compounds of formula I,

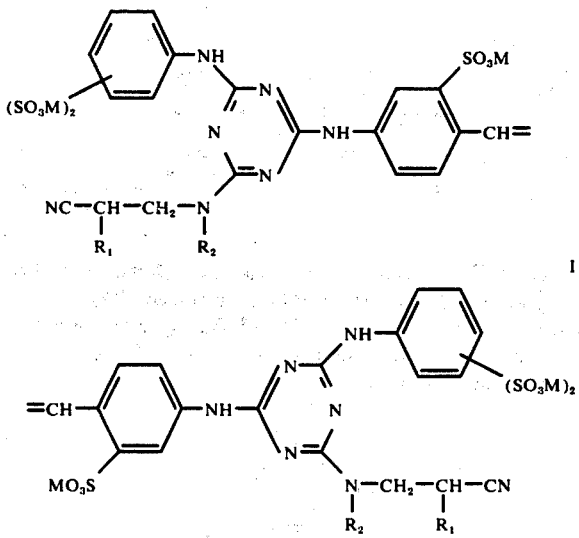

In the compounds of formula I, any alkyl or alkoxy radical as a substituent on any benzyl radical is preferably of 1 to 4, more preferably of 1 or 2, carbon atoms, the most preferred such radicals being methyl and methoxy. Any halogen as a substituent on any benzyl radical may, for example, be fluorine, chlorine or bromine, chlorine being the preferred halogen. Any benzyl radical is preferably unsubstituted or mono-substituted, the substituent preferably being in ortho- or para-position to the methylene group.

Any alkyl radical as substituent on any cyclohexyl radical is preferably of 1 to 4 carbon atoms, more preferably of 1 or 2 carbon atoms. As examples of alkyl substituted cyclohexyl radicals may be given ethylcyclohexyl and mono-, di- and tri-methylcyclohexyl. Any cyclohexyl radical is preferably unsubstituted or substituted by 1, 2 or, preferably, 3 methyl groups.

Where $R_2$ signifies $C_{1-6}$alkyl, such is preferably $C_{1-4}$alkyl.

$R_1$ preferably signifies hydrogen.

Where M signifies a cation, the exact nature thereof is not critical provided it is non-chromophoric. Cations conventional in the optical brightener art, to which the present invention relates, may be employed. As examples of preferred cations may be given the alkalimetal cations, such as of sodium, potassium or lithium, the alkaline-earth metal cations, such as of magnesium or calcium, or aluminium, or ammonium, alkylammonium and substituted alkylammonium cations, e.g. of formula $R_{10}R_{11}R_{12}N^+H$, where $R_{10}$, $R_{11}$ and $R_{12}$, independently, signify hydrogen or $C_{1-4}$alkyl, unsubstituted or substituted by up to two, preferably one, hydroxy group, e.g. mono- di- or triethanolammonium and mono-, di- or triisopropanolammonium cations. The most preferred cation, from an economical and production standpoint, is the sodium cation. In the formulae used herein, for the sake of simplicity, M is shown to be monovalent. As will be appreciated, it may be di- or polyvalent, e.g. di-valent when an alkaline earth metal cation and tri-valent when an aluminium cation.

Of the $—SO_3M$ groups in the terminal anilino groups, one is preferably in the ortho-position, the other in the meta-position.

As a preferred group of compounds may be given the compounds of formula Ia,

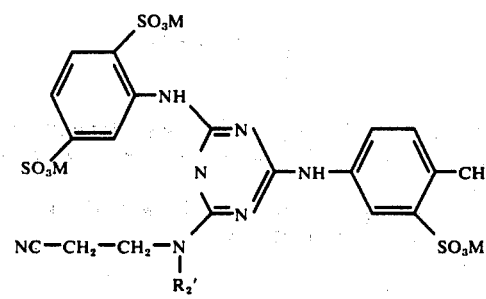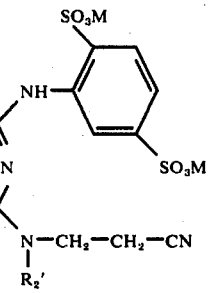

in which
  the $R_1$'s are the same and signify hydrogen or methyl,
  the $R_2$'s are the same and signify hydrogen; $C_{1-6}$alkyl; cyclohexyl, unsubstituted or substituted by up to three $C_{1-6}$alkyl radicals; or benzyl, unsubstituted or substituted by up to two substituents selected from halogen, $C_{1-6}$alkoxy and $C_{1-6}$alkyl, and
  the M's signify hydrogen or a nonchromophoric cation.

in which
  the $R_2'$'s, which are the same, signify $C_{1-4}$alkyl, unsubstituted benzyl, unsubstituted cyclohexyl or 3,3,5-trimethylcyclohexyl, and
  M is as defined above.

Especially preferred compounds are the compounds of formula Ia, in which $R_2'$ signifies methyl or benzyl.

The invention also provides a process for the production of compounds of formula I, characterized by reacting, in any desired order,
  a. a cyanuro halide with
  b. a compound of formula II,

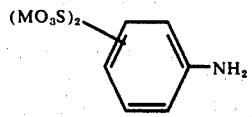

in which M is as defined above,
  c. a diamine of formula III,

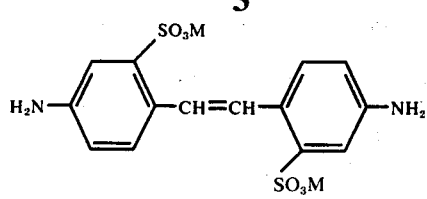

III in which M is as defined above, and
d. a compound of formula IV,

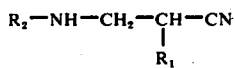  IV in which $R_1$ and $R_2$ are as defined above.

The process is conveniently carried out in conventional manner.

It is preferred to employ a mol ratio of cyanuro halide: compound II: compound III: compound IV of 2:2:1:2.

The preferred cyanuro halides are the bromide and chloride, particularly the latter.

The reaction may be carried out in aqueous medium, the cyanuro halide being suspended in water; or in an aqueous organic medium, the cyanuro halide being

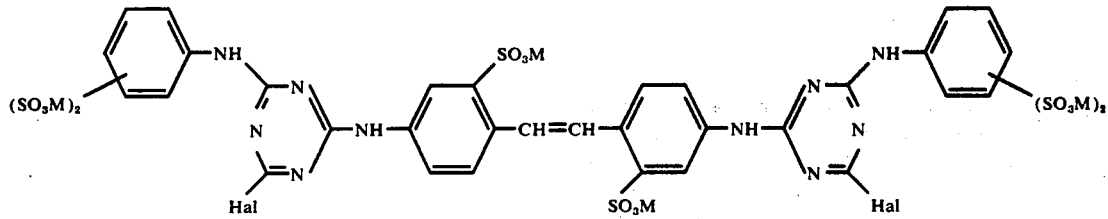

dissolved in an organic solvent, such as in acetone, benzene, toluene or chlorobenzene and an aqueous solution or suspension of the respective amine being added thereto. The reaction is accelerated and purer products obtained by the addition of a dispersing agent to the reaction mixture.

For substitution of the first halogen of the cyanuro halide, it is preferred to operate at a temperature of from 0° to 150° C and at a pH of from 1 to 7. For substitution of the second halogen of the cyanuro halide it is preferred to operate at from 20° to 60° C under weakly acid to weakly alkaline conditions e.g. at pH from 4 to 8. For substitution of the third halogen of the cyanuro halide, it is preferred to operate at temperatures of from 60° to 100° C and at pH of from 4 to 10.

The hydrochloric acid freed in the course of the reaction is preferably neutralised, e.g. using alkali-metal hydroxides, bicarbonates or carbonates, or tertiary organic amines, e.g. tris-(2-hydroxyethyl)-amine.

The respective three last steps of the process, which form a part of the invention, may be summarised as follows:

a. reacting a compound of formula II, stated above, with a compound of formula V,

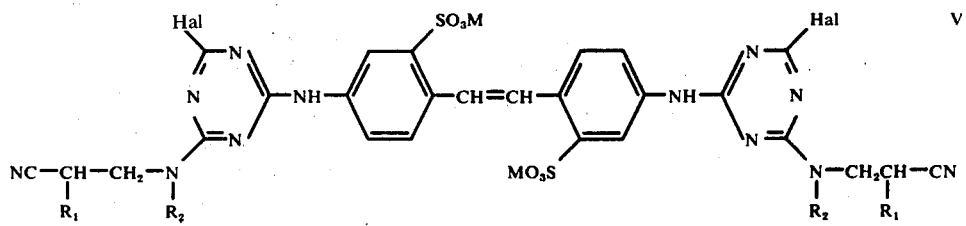

in which $R_1$, $R_2$ and M are as defined above, and Hal signifies halogen, preferably bromine or chlorine, the mol ratio of compound II to V being preferably 2:1 b. reacting a compound of formula III, above, with a compound of formula VI,

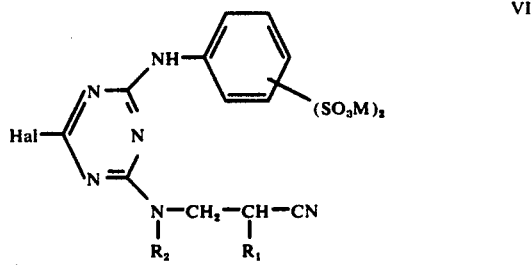

in which $R_1$, $R_2$, M and Hal are as defined above, the mol ratio of compound III to compound VI preferably being 1:2, or c. reacting a compound of formula IV, above, with a compound of formula VII, in which M and Hal are as defined above, the mol ratio of compound IV to compound VII preferably being 2:1.

The compounds of formula IV may be obtained by reacting an amine of formula VIII, $R_2 - NH_2$  VIII in which $R_2$ is as defined above, with a nitrile of formula XI,

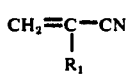  XI in which $R_1$ is as defined above, at 0° to 100° C in conventional manner.

The compounds of formulae II, III, VIII and XI are either known or may be obtained in conventional manner from available starting materials.

The resulting compounds of formula I may be isolated and purified in conventional manner, e.g. salting out, precipitation by addition of acids or by evaporation.

The compounds of formula I are indicated for use as optical brightening agents, particularly for the optical brightening of cellulosic substrates. The cellulose substrate may, for example, be in such forms as loose fibre, thread, yarn, fabric, knit fabric, non-woven fabric, paper, felt, velvet or carpet forms etc. optionally in mixture with other fibres or as homogeneous mass, e.g. viscose. Particularly, the substrate may be finished or permanently finished during the brightening process. Particular applications of the compounds of formula I are as follows:

A. the brightening of cellulosic textiles, particularly cotton, from a long bath, B. the brightening of cellulosic textiles, particularly cotton, according to a padding process (especially continuous padding process), C. the brightening and simultaneous finishing of cellulosic textiles, particularly cotton, in a synthetic resin bath, D. the optical brightening of viscose rayon by employing the compounds of formula I in the spinning mass during the production process, E. the optical brightening of papers in the stock, or surface treatment of the formed papers.

The compounds of formula I are especially suitable for applications (C) and (E), particularly for the surface treatment of the formed papers.

The compounds of formula I, particularly the alkali metal salts thereof, are well soluble in water. Comparatively high concentrated liquid preparations (e.g. 10 to 30%) may be produced therewith, e.g. with a solvent aid, such as glycol, glycolic ether, formamide, acetamide, urea, or mono-, di- or tris-(2-hydroxyethyl)- or -(2-hydroxypropyl)-amine. This property is advantageous in the application of optical brightening agents. The compounds may be used according to any desired process suitable for the substrates being brightened.

When using the compounds from a long bath, 0.05 to 0.8% of the optical brightener, in relation to the substrate, are preferably used. The bath length is preferably in a ratio of 1:10 to 1:50 and the treatment temperature in the range of 30° to 60° C. The bath may contain further assistants, e.g. exhaust assistants.

Due to their low substantivity, the compounds of formula I are suitable as brightening agents for padding processes, particularly continuous padding processes, where the brightening concentration in the treatment bath may be kept almost constant. The concentration of the optical brightener is preferably from 0.02 to 1.2%, conveniently from 0.05 to 0.8%, in relation to the substrate. The brightener may be fixed in accordance with the cold retention process or by application of heat, optionally after intermediate drying. In the finishing of textiles (fabrics or non-woven fabrics) with binding agents, especially synthetic resins, the optical brightener may be added to the synthetic resin either in the treatment bath or before. Advantageously, 0.02 to 1.2%, preferably 0.05 to 0.8% of optical brightener, in relation to the substrate, are added. The brightener may be fixed and the finishing agent cross-linked in accordance with the cold store or cold cross-linking process, or by heat treatment, optionally after intermediate drying. Due to their stability in a strongly acid bath and towards salts, such as magnesium chloride and zinc chloride, the compounds of formula I are eminently suitable for the optical brightening and simultaneous crease-proof finish of cotton.

Further, the compounds of formula I are suitable for the brightening of paper. For the brightening of paper in the stock they are preferably used in the range of 0.01 to 0.5%, based on air-dried cellulose.

The compounds of formula I are also suitable for the brightening of the paper surface after sheet formation. This may be effected by adding the optical brightener to the coating pastes, sizing solutions or suspensions (size press) or merely by applying dilute solutions to the paper.

The paper may be of fine or coarse nature and of bleached or unbleached cellulose.

For the treatment of paper in the size press, sizing liquors containing, per liter of the treatment liquor, 0.3 to 8, preferably 0.5 to 6g of the optical brightener, may be used. The amount of the brightener can of course be chosen to suit the nature and amount of the binding agent used, the paper and the degree of whiteness required. The concentration of the binding agent is usually from approximately 2 to 15% of the bath. Optical brightening liquors for surface application to paper may contain further additives, e.g. white pigments or fillers, these being normally employed in amounts of approximately 10 to 65%, based on the coating paste. The binding agents are used in amounts of approximately 5 to 25%. The optical brightener is preferably used in amounts of about 0.3 to 6 g per liter of coating paste.

By the addition of polyvinyl alcohol and/or polyethylene glycol as blending agent for liquid preparations or powder formulations of the optical brighteners, their white effect may be considerably increased. Appropriate binding agents are, for example, decomposed starch, alginates, gelatine, polyvinyl alcohol, polyvinyl pyrrolidone, carboxymethyl cellulose, casein, protein, polyvinylidene chloride and mixtures of these binding agents, the decomposed starch, the polyvinyl alcohol and the carboxy methyl cellulose being preferred. Also suitable are aqueous synthetic resin dispersions based on co-polymers of acrylic or butadiene styrene resins, the content of synthetic resin being approximately 50%.

Appropriate fillers and white pigments are the common products such as China-Clay, calcium carbonate, "satin white", "Blancfix", titanium oxide, talc, precipitated aluminium silicates etc. as well as the mixtures thereof.

The coating pastes may additionally contain hydrosoluble poly- or metaphosphates and, as wetting agents, unsulphated or sulphated higher alkanol or alkylphenol polyglycolic ethers of 8 to 14 alkyl carbon atoms and 1 to 20 ethylene oxide groups. In order to obtain good flow properties, an alkali coating paste is preferably used for the pigment coating. The alkaline reaction is conveniently effected with ammonium hydroxide or with sodium or potassium hydroxides, -carbonates, -borates, -perborates or mixtures thereof.

The compounds of formula I show acid and salt resistance. They are particularly resistant towards the action of aluminium ions and are well compatible with binding agents and fillers used for the surface finishing of papers. The resulting optical brightenings, especially brightenings on paper, show an intensely white shade.

In the following Examples the parts, unless otherwise stated, are by weight and the percentages likewise. The temperatures are in degrees centigrade. The parts by weight relate to the parts by volume as grams to milliliters.

EXAMPLE 1

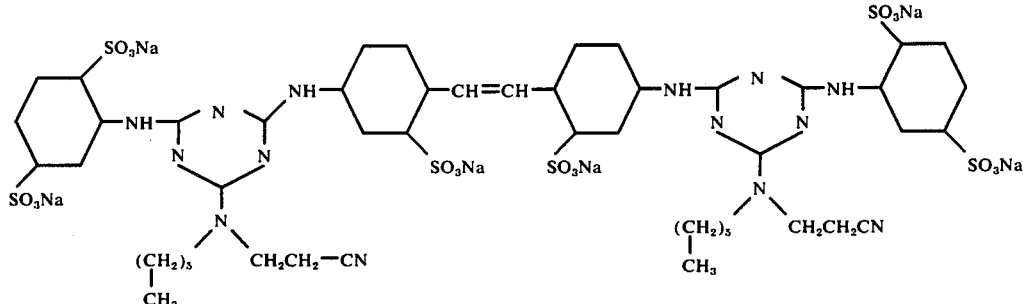

A solution of 190 parts of cyanuro chloride in 800 parts by volume of acetone is run with stirring, over the course of 10 minutes, into 5000 parts of ice water. A solution of 253 parts of aniline-2,5-disulphonic acid and 106 parts of calcinated soda in 1500 parts of water is added dropwise at 0° to 5° over the course of 1 hour and with stirring. The pH is kept at 3 to 4 by the dropwise addition of 15% soda solution. The suspension is thus slowly dissolved. The solution is stirred at 0° to 5° until no primary, aromatic amino groups may be detected any longer by the diazo reaction. A solution of 185 parts of 4,4'-diaminostilbene-2,2'-disulphonic acid and 106 parts of calcinated soda in 1500 parts of water are subsequently added, the pH is adjusted to 7 by the addition of 15% soda solution and the solution is heated to 30° until the diazo reaction turns negative. 216 Parts of β-hexylamino propionitrile are aded to the clear solution, the pH is increased to 9 to 10 by the addition of 15% soda solution and the solution is slowly heated to 95°–100° with distillation of the acetone. The solution is boiled at reflux over the course of 1½ hours, the pH being kept at 9 to 10 by the addition of soda solution. 720 Parts of sodium chloride are subsequently added to the clear solution which is then allowed to cool. The greenish yellow product precipitates, is suction filtered and dried under vacuum.

The above β-hexylamino-propionitrile is obtained by adding with stirring 74 parts of acrylonitrile to 142 parts of n-hexylamine at 30° and stirring the mixture at this temperature for a further 2 hours.

Similar brighteners are obtained by replacing 216 parts of β-hexylamino-propionitrile by 98 parts of β-amino-propionitrile or 118 parts of β-methyl-amino-propionitrile or 137 parts of β-ethyl-amino-propionitrile or 157 parts of β-propylamino-propionitrile or 177 parts of β-butyl-amino-propionitrile or 196 parts of β-pentylamino-propionitrile.

The same result is obtained by replacing the aniline-2,5-disulphonic acid by the isomeric aniline-2,4-disulphonic acid or the isomeric aniline-3,5-disulphonic acid.

In the following Table further brighteners according to the invention, of formula

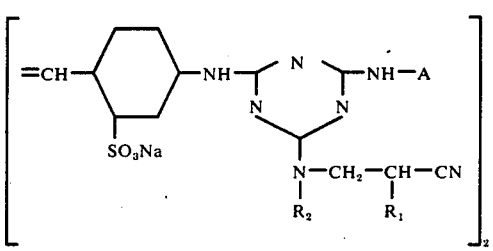

are obtained.

| Exp. No. | A | $R_1$ | $R_2$ |
|---|---|---|---|
| 2 | 2,5-disulphophenyl | H | H |
| 3 | '' | H | $CH_3-$ |
| 4 | '' | H | $CH_3CH_2-$ |
| 5 | '' | H | $CH_3(CH_2)_2-$ |
| 6 | '' | H | $CH_3(CH_2)_4-$ |
| 7 | '' | H | ⌬—$CH_2-$ |
| 8 | '' | H | Cl—⌬—$CH_2-$ |
| 9 | '' | H | $CH_3$—⌬—$CH_2-$ |
| 10 | '' | H | $CH_3O$—⌬—$CH_2-$ |
| 11 | '' | H | ⌬(Cl)—$CH_2-$ |
| 12 | '' | H | ⌬($CH_3$)—$CH_2-$ |
| 13 | '' | H | ⌬($OCH_3$)—$CH_2-$ |
| 14 | '' | H | ⌬(H) |
| 15 | '' | H | ⌬($CH_3$, H, $CH_3$, $CH_3$) |
| 16 | '' | $CH_3-$ | H |
| 17 | '' | $CH_3-$ | $CH_3-$ |
| 18 | '' | $CH_3-$ | $CH_3CH_2-$ |
| 19 | '' | $CH_3-$ | $CH_3(CH_2)_2-$ |
| 20 | '' | $CH_3-$ | $CH_3(CH_2)_4-$ |
| 21 | 2,4-disulphophenyl | H | H |
| 22 | '' | H | $CH_3-$ |
| 23 | '' | H | $CH_3CH_2-$ |
| 24 | '' | H | $CH_3(CH_2)_2-$ |
| 25 | '' | H | $CH_3(CH_2)_4-$ |

-continued

| Exp. No. | A | R | R |
|---|---|---|---|
| 26 | " | H | C6H5-CH2- |
| 27 | " | H | Cl-C6H4-CH2- |
| 28 | " | H | CH3-C6H4-CH2- |
| 29 | " | H | CH3O-C6H4-CH2- |
| 30 | " | H | 2-Cl-C6H4-CH2- |
| 31 | " | H | 2-CH3-C6H4-CH2- |
| 32 | " | H | 2-OCH3-C6H4-CH2- |
| 33 | " | H | cyclohexyl |
| 34 | " | H | 2,6,6-trimethylcyclohexyl |
| 35 | 3,5-disulphophenyl | H | H |
| 36 | " | H | CH3- |
| 37 | " | H | CH3CH2- |
| 38 | " | H | CH3(CH2)2- |
| 39 | " | H | CH3(CH2)4- |
| 40 | " | H | C6H5-CH2- |
| 41 | " | H | Cl-C6H4-CH2- |
| 42 | " | H | CH3-C6H4-CH2- |
| 43 | " | H | CH3O-C6H4-CH2- |
| 44 | " | H | 2-Cl-C6H4-CH2- |
| 45 | " | H | 2-CH3-C6H4-CH2- |
| 46 | " | H | 2-OCH3-C6H4-CH2- |
| 47 | " | H | cyclohexyl |
| 48 | 3,5-disulphophenyl | H | 2,6,6-trimethylcyclohexyl |
| 49 | 2,4-disulphophenyl | CH3- | H |
| 50 | " | CH3- | CH3- |
| 51 | " | CH3- | CH3CH2- |
| 52 | " | CH3- | CH3(CH2)2- |
| 53 | " | CH3- | CH3(CH2)4- |
| 54 | 3,5-disulphophenyl | CH3- | H |
| 55 | " | CH3- | CH3- |
| 56 | " | CH3- | CH3CH2- |
| 57 | " | CH3- | CH3(CH2)2- |
| 58 | " | CH3- | CH3(CH2)4- |

Application Example A

A cotton fabric is drawn through a bath containing
 240 parts of a synthetic resin precondensate, e.g. dimethylol ethylene urea,
 28 parts of sulphuric acid 40° Be
 2 parts of a brightener of Example 3
 730 parts of water,
expressed between two rollers to a pick up of 100% and dried at 90° until a residual humidity of 8% is obtained. The fabric is subsequently rolled up and stored at room temperature over the course of 17 hours. It is cold rinsed, cold neutralized with a solution of 2g/l of soda, cold rinsed, expressed and dried at 100°. The fabric treated in this way shows a good brilliant brightening of neutral shade.

Application Example B

A cotton fabric is drawn through a solution, containing 8 parts of a brightener of Example 5 in 1000 parts of solution, expressed to a pick up of 100% and dried at 60°-70°. The fabric shows a good brightening. The brightening effect is considerably increased by adding 8 parts of a polyethylene glycol (with a molecular weight of 5000 to 6000).

Application Example C

A sized paper of sulphite cellulose is coated with a coating paste consisting of
 66 parts of kaolin
 33 parts of water
 10 parts of a 50% dispersion of a butadiene-styrene-copolymer
 5 parts of a 10% casein solution
 0.3 part of a 10% solution of a brightener of Example 7.

The degree of whiteness is considerably higher than that of an unbrightened coating paste. The effect is considerably improved by adding to the coating paste 1 part of a 10% solution of a polyethylene glycol having a molecular weight of 5000 to 6000.

Application Example D

To a suspension of 100 parts of bleached sulphite cellulose in 4000 parts of water, ground in a hollander engine to 40° Schopper-Riegler and containing 10 parts of aluminium sulphate, is added a solution of 0.3 part of a brightener of Example 10 in 300 parts of water. The solution is carefully mixed over the course of 30 minutes. The cellulose mass is subsequently sized in conventional manner with 20 parts of a 10% colophonium resin size and 3 parts of aluminium sulphate, dissolved in 10 parts of water. The mass is then diluted with water to 20,000 parts and processed into paper sheets.

The paper thus produced shows a good brightening. The result indicates that the brighteners produced in accordance with the invention may also be used in the paper mass at low pH values. This is of importance for the paper production as the process has to be effected with backwater which contains plenty of aluminium sulphate.

Application Example E

A coating mass consisting of
66 parts of kaolin
33 parts of water
10 parts of a 50% dispersion of a butadiene-styrene copolymer
1 part of a 10% solution of a polyethylene glycol having a molecular weight of 5000 to 6000
0.3 parts of a 10% solution of a brightener of Example 14,
is applied by means of a coating apparatus to a sized paper consisting of 50% of bleached sulphite cellulose and 50% of mechanical wood pulp. A paper with an excellent brightening effect is obtained.

5 Parts of a 10% solution of a decomposed starch may furthermore be added to the above-mentioned coating paste. The brightening effect is thus slightly improved.

Application Example F

A bleached cotton fabric, prepurified by conventional methods, is impregnated on a padder with a chemical finishing bath of room temperature, containing, per liter, the following constituents: 70 g of dimethylolpropylene urea, 6 g of the brightening agent of Example 8 and 20 g of magnesium chloride hexahydrate.

The impregnated goods are expressed to a pick up of 100%, dried at 100° for 30 seconds and subsequently condensed on a stenter at 160° over the course of 5 minutes. The fabric obtained in accordance with this process shows a crease-resistant finish and a high degree of whiteness.

In place of dimethylolpropylene urea there may also be used as crease-proof chemical finish, dimethylolethylene urea or dimethyloldihydroxyethylene urea or dimethylolmethyl carbamate. Apart from magnesium chloride also zinc nitrite or zinc chloride may be used as catalysts. The finished fabrics show also a high degree of whiteness.

Application Example G

A bleached cotton fabric is drawn through an aqueous bath containing
300 g/l of a synthetic resin precondensate based on dimethylol dihydroxyethylene urea,
160 g/l of hydrochloric acid (concentrated)
5 g/l of a brightener of Example 2,
and expressed to a pick up of 100%. The fabric is subsequently rolled up, rotated and stored at room temperature over the course of 17 hours. It is then cold rinsed, neutralized with a solution of 2g/l of soda, acidified again with 1g/l of acetic acid, rinsed to neutral, expressed and dried on the stenter at 100° for 30 seconds. The fabric treated in this way shows a strong brightening effect.

Application Example H

A cotton-cretonne fabric is drawn through an aqueous bleaching bath containing
40 g/l of 35% hydrogen peroxide
30 g/l of sodium hydroxide solution 36° Be
15 g/l of silicate of soda 38° Be
5 g/l of stabilizer
9 g/l of the brightener of Example 3,
and expressed to a pick up of 100%. The fabric is rolled up and stored while rotating at room temperature over the course of 17 hours. The fabric is then rinsed with water at 90°, acidified with 2 g/l of acetic acid and cold rinsed until the fabric reacts neutrally. Subsequently, it is expressed and dried at 100° for 30 seconds. The fabric treated in this way shows a strong brightening effect of bluish shade.

Application Example J

60 Parts of decomposed starch are stirred in the cold into 600 parts of water and dissolved at 80°–90°. To this solution are added 3 parts of sodium polyphosphate, 120 parts of a butadiene-styrene co-polymer, a solution of 4 parts of the brightener of Example 1 in 400 parts of water and 600 parts of white pigment (kaolin). A sized raw paper, consisting of 50% of bleached sulphite cellulose and 50% of mechanical wood pulp, is coated with this mass by means of a coating apparatus. An intensely white paper with fastness to print is obtained. The brightening effect is considerably increased by the addition of 4 parts of polyvinyl alcohol to the coating mass.

What is claimed is:
1. A compound of formula I,

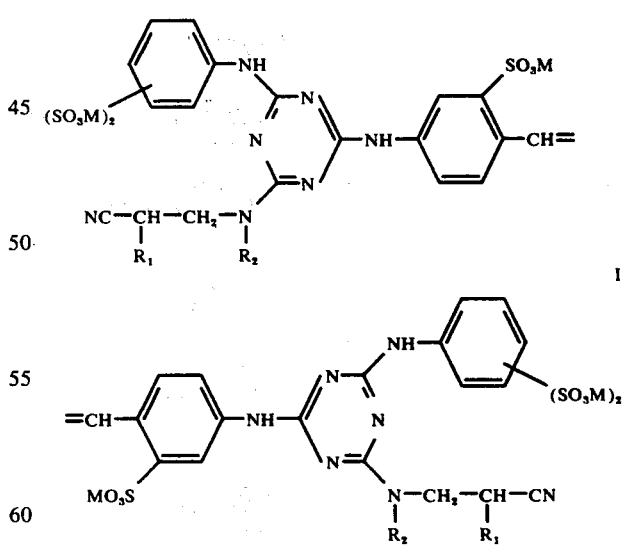

wherein
the $R_1$'s are the same and signify hydrogen or methyl,
the $R_2$'s are the same and signify hydrogen or $C_{1-4}$ alkyl, and
the M's signify hydrogen or a non-chromophoric cation.

2. A compound of claim 1, wherein $R_2$ signifies methyl.

3. A compound of claim 1, wherein $R_1$ signifies hydrogen.

4. A compound of claim 1, wherein, of the $-SO_3M$ groups in the terminal anilino groups, one is in the o-position, the other in the meta position.

5. A compound of claim 4, of formula Ia,

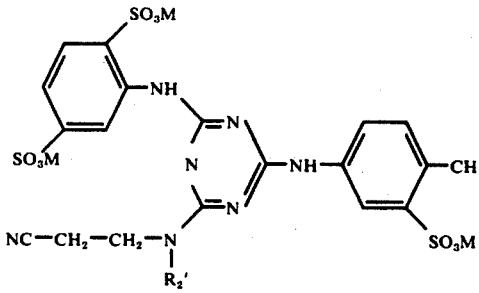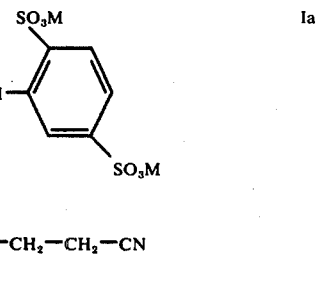

Ia wherein
the $R_2'$'s are the same and signify $C_{1-4}$alkyl, and M is as defined in claim 14.

6. A compound of claim 5, wherein the $R_2'$ 's signify methyl.

7. A compound of claim 1, wherein M signifies hydrogen, an alkali metal, alkaline earth metal or aluminium cation or a cation of formula $R_{10}R_{11}R_{12}N^+H$, where $R_{10}$, $R_{11}$, $R_{12}$, independently, signify hydrogen or $C_{1-4}$alkyl, unsubstituted or substituted by up to two hydroxy groups.

8. A compound of claim 7, in which any cation as M is the sodium ion.

* * * * *